United States Patent [19]

Calzi et al.

[11] Patent Number: 5,238,853
[45] Date of Patent: Aug. 24, 1993

[54] PROCESS AND APPARATUS FOR THE ELECTROCHEMICAL DETERMINATION OF OXYGEN IN A BLOOD GAS ANALYZER

[75] Inventors: Claudio Calzi; Gabrio Tancredi, both of Milan, Italy

[73] Assignee: Instrumentation Laboratory S.R.L., Milan, Italy

[21] Appl. No.: 758,826

[22] Filed: Sep. 11, 1991

[30] Foreign Application Priority Data

Sep. 14, 1990 [IT] Italy ................. 21474 A/90

[51] Int. Cl.$^5$ ............................................. G01N 33/50
[52] U.S. Cl. ........................................ 436/68; 436/52; 436/63; 422/81; 422/82.01; 422/82.03; 422/82.04; 204/153.17; 204/403; 204/415
[58] Field of Search ................. 422/79, 80, 81, 82.01, 422/82.02, 82.03, 82.04, 68.1; 436/52, 62, 63, 68; 204/415, 153.17, 403

[56] References Cited

U.S. PATENT DOCUMENTS

| | | | |
|---|---|---|---|
| 3,526,481 | 9/1970 | Rubricius | 422/82.03 X |
| 3,614,856 | 10/1971 | Sanz et al. | 436/68 X |
| 3,868,223 | 2/1975 | Robock et al. | 422/79 |
| 4,209,300 | 6/1980 | Thibault | 422/82.04 X |
| 4,221,567 | 9/1980 | Clark et al. | 422/82.04 X |
| 4,293,307 | 10/1981 | Simpson et al. | 204/415 X |
| 4,413,147 | 11/1983 | Khoobiar | 568/475 X |
| 4,504,443 | 3/1985 | Hansen et al. | 436/52 X |
| 4,516,580 | 5/1985 | Polanyi | 436/68 X |
| 4,541,901 | 9/1985 | Parker et al. | 204/415 X |
| 4,594,326 | 6/1986 | Wade | 436/52 X |
| 4,844,097 | 7/1989 | Bellhouse et al. | 436/68 X |
| 5,017,496 | 5/1991 | Klapwijk et al. | 422/79 X |

Primary Examiner—Jill A. Johnston
Assistant Examiner—Maureen M. Wallenhorst
Attorney, Agent, or Firm—Testa, Hurwitz & Thibeault

[57] ABSTRACT

In a blood gas analyzer, a substantially oxygen-free measurement solution is fed through a measuring cell as far as a diffusion cell in which the measurement solution is brought into contact with a blood sample to be tested. The gases dissolved in the blood sample diffuse through a membrane in the diffusion cell into the solution. The measurement solution is then propelled in the reverse direction to feed into the measuring cell. In the measuring cell, the measurement solution is electrochemically measured to determine a value which is related to the partial pressure of oxygen ($pO_2$) in the sample.

14 Claims, 4 Drawing Sheets

PROCESS AND APPARATUS FOR THE ELECTROCHEMICAL DETERMINATION OF OXYGEN IN A BLOOD GAS ANALYZER

This invention relates to improvements in the electrochemical determination of the blood partial pressure of oxygen in a blood gas analyzer apparatus. A blood gas analyzer is a diagnostic apparatus which measures the partial pressure of gaseous $O_2$ and $CO_2$ in the venous, arterial or mixed blood and the blood pH.

Apparatus of this type is normally used in central hospital laboratories, in resuscitation centers, etc., and is indispensable in certain surgical circumstances, its function not being able to be performed by other instruments.

In this respect, measuring these basic parameters enables a variety of derived parameters to be obtained, particularly important among which is the acid-base equilibrium (an indicator of renal and pulmonary operation).

Most of the oxygen measurement systems used in current blood gas analyzers are based on the classic Clark electrode. The measurement system used with this latter is a polarographic system and is based on a platinum cathode and a silver/silver chloride anode. A membrane of polypropylene or other oxygen-permeable material separates the blood sample from the measuring system.

The oxygen which diffuses through the membrane is reduced at the cathode when an adequate potential (typically 0.7 V) is applied between the anode and the cathode (so-called polarization voltage).

With a platinum cathode connected to a silver/silver chloride anode, 4 electrons are produced at the anode and are used at the cathode to reduce one molecule of oxygen on the basis of the following reactions:

| anode | $4Ag + 4Cl \rightarrow 4AgCl + 4e-$ |
| cathode | $4H+ 4e- + O_2 \rightarrow 2H_2O$ |

The current developed by these two reactions is proportional to the $pO_2$ of the blood sample to be tested.

Technological development in recent years has been applied to many aspects of this equipment for the purpose of simplifying use and increasing automation and reliability. In spite of this, a blood gas analyzer is a complicated and delicate instrument which requires extensive maintenance on its electrochemical sensors for correct operation.

This derives mainly from the fact that the constituent parts of the electrochemical sensors of a blood gas analyzer are not subject to sudden failure, but because of their nature undergo progressive degradation with time, thus requiring frequent and careful maintenance.

The problems which chronically afflict these sensors can be summarized as follows:
aging of the oxygen-permeable membrane with loss of elasticity;
electrolyte alteration in terms of concentration variation and/or insufficient self-change;
trapping of protein substances in the oxygen-permeable membrane.

The object of the present invention is therefore to provide a system for the electrochemical determination of oxygen partial pressure which overcomes the drawbacks of known apparatus and processes, so resulting in high reliability and requiring practically no ordinary maintenance, but without leading to any appreciable fall-off in the apparatus performance between the programmed shut-downs for replacing those parts of the apparatus which by their nature have a limited life.

A general object of the invention is to restore the apparatus to constant controlled initial conditions after each measurement, this expedient being considered essential for obtaining reproducible and reliable measurements.

A further object of the invention is to enable the proper operation of the entire apparatus to be checked simply by checking the time interval between the successive measurements on the various samples.

SUMMARY OF THE INVENTION

To this end the invention provides a process for obtaining the value of an electrical quantity related to the $pO_2$ and propelling it along a fluid circuit to pass in succession through a measuring cell for determining the value of the electrical quantity, and a diffusion cell in which the measurement solution is brought into contact with the blood sample tested via a permeation membrane which allows gases to diffuse but not ions, then halting the flow of measurement solution to allow the gases dissolved in the sample to diffuse through the membrane, then propelling the measurement solution in the reverse direction through the circuit so that the measurement solution which has remained static in the diffusion cell is transferred to the measuring cell, then measuring the value of the electrical quantity related to the $pO_2$.

The apparatus according to the invention comprises a fluid circuit starting from a source of measurement solution with substantially zero $pO_2$ and passing in succession through a measuring cell able to provide the value of an electrical quantity related to the $pO_2$ of the solution passing through the cell, and a diffusion cell in which the solution is brought into contact with the blood sample via a permeable membrane, the circuit terminating at discharge, means also being provided for propelling the solution in both directions within the circuit, for propelling the solution from the secure to the diffusion cell via the measuring cell, for halting its flow for a predetermined time, and for propelling the solution in the reverse direction to transfer the quantity held in the diffusion cell into the measuring cell, means being provided for measuring the value of the electrical quantity of the solution flowing into the measuring cell.

BRIEF DESCRIPTION OF THE DRAWING

The objects and characteristics of the present invention will be more apparent from the description of an embodiment thereof given hereinafter with reference to the accompanying drawings, in which.

DETAILED DESCRIPTION

Figure 1:
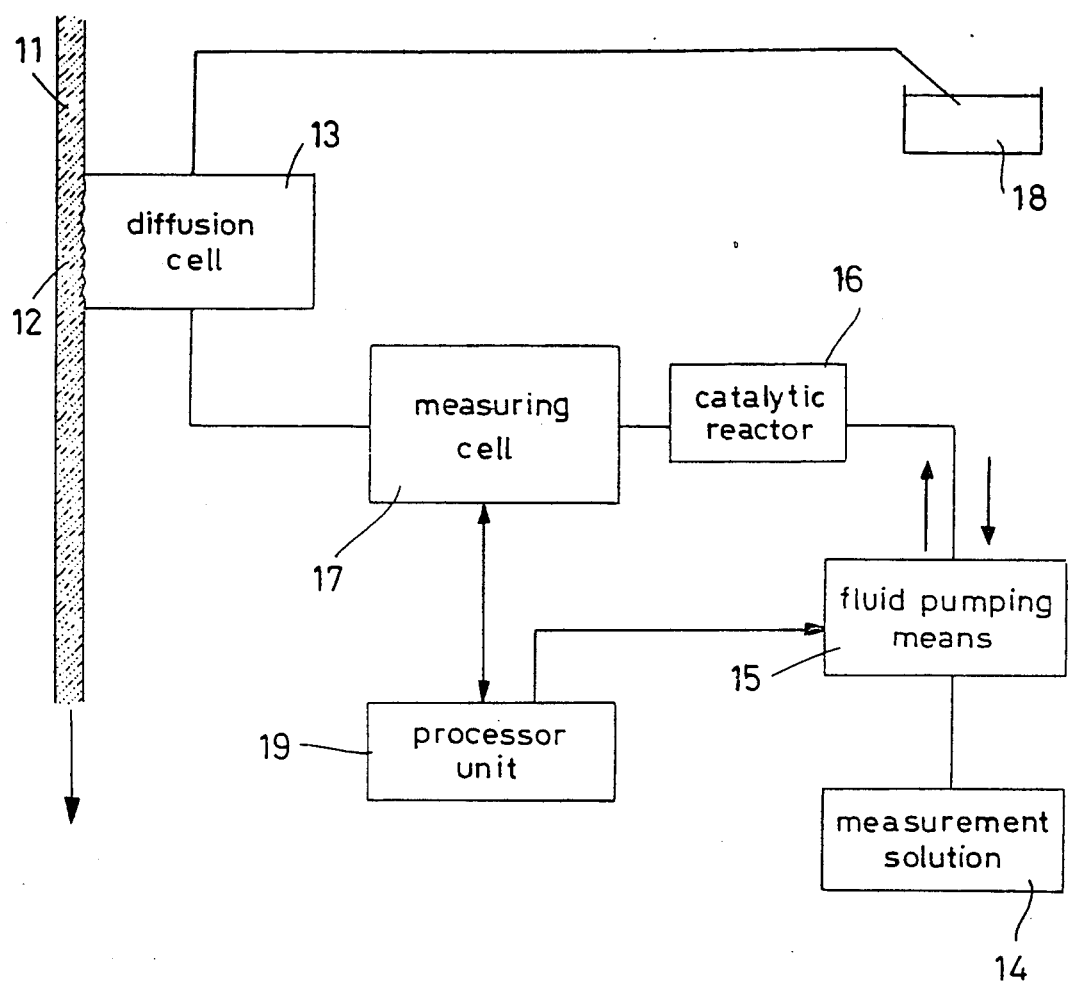
FIG. 1 is an outline scheme of the system according to the invention.

The apparatus shown in FIG. 1 comprises a duct to receive the blood sample of which the $pO_2$ is to be measured, and communicating via a permeating membrane 12 with a diffusion cell 13 forming part of a fluid circuit through which a measurement solution passes. This circuit starts at a container 14 for the measurement solution and comprises in succession fluid pumping means 15, a reactor 16 in which the $pO_2$ is reduced to substantially zero, and a measuring cell 17.

From the diffusion cell 13 the circuit terminates at discharge, indicated schematically at 18.

Examining the components of the apparatus in detail, the fluid pumping means 15 can consist of metering pumps of known types for feeding controlled quantities of measurement solution into the circuit to enable predetermined quantities of measurement solution into the circuit to enable predetermined quantities of solution to selectively reach the various units provided in the circuit. Such metering pump 15 can be totally controlled by a data processor unit 19 which implements the sequential execution of the operations required by the measurement process by sequentially operating the means provided for this purpose, such as the pumping unit 15 and the sensors of the measuring cell 17. The unit 19 also processes the data received from the sensors of the measuring cell 17 and controls or enables the various sequential operations while at the same time handling the various measurements. The process unit 19 will not be further described as it can be formed in various known ways.

The reactor 16 can be of any type suitable for conducting a reaction in which dissolved oxygen is removed from the measurement solution. In particular, the catalytic reactor 16 can consist of a stainless steel chromatographic column fitted with gas-tight connectors and packed with granular catalyst material. In each example that follow, a column of 5 cam length and 4 mm inside diameter (tapering to 0.8 mm inside diameter at its outlet) was packed with approximately 0.75 of platinum on aluminum catalyst, sandwiched within the column between porous stainless steel discs.

As temperature variations influence the measured values, between the catalytic reactor 16 and the measuring cell 17 there is provided a system of the known art (not shown in FIG. 1) for the temperature control of the electrolyte, enabling a constant temperature of about 37° C. (normal body temperature) to be maintained.

For the purposes of the invention, the container 14 and the reactor 16 are to be considered as simply forming a source of oxygen-free measurement solution, and this source can assume any form available to the known art.

The measuring cell 17 is for example of the thin layer voltametric type.

The diffusion cell 13 is to be considered a totally known unit in terms of its concept, in that it is merely required to bring the measurement solution into contact with the sample flowing through the duct 11, via a permeation membrane 12 which allows gases to diffuse between the two liquids but does not allow ions to pass.

The measurement process using the described apparatus is conducted in the following manner. When the sample to be analyzed is introduced into the duct 11, the pump 15 feeds a quantity of solution into the circuit, so that oxygen-free solution reaches the diffusion cell. During this stage, the solution quantity contained in the diffusion cell on commencement of measurement, and which is contaminated by oxygen which may have passed through the membrane from the air contained in the duct 11 before introduction of the sample, is fed to discharge.

It should be noted that during this stage in which the measurement liquid is being fed into the diffusion cell the measuring cell can be used to measure the $pO_2$ of the solution. Any contamination of the liquid, or indeed any accidental lack of liquid, would be immediately signalled as a warning of the impossibility of the measurement which is to be made. When a quantity of oxygen-free solution has reached the diffusion cell 13, the flow is halted for a determined time. $O_2$ necessarily diffuses from the sample to the measurement solution, this diffusion being a function of the $pO_2$ in the sample.

Figure 2:
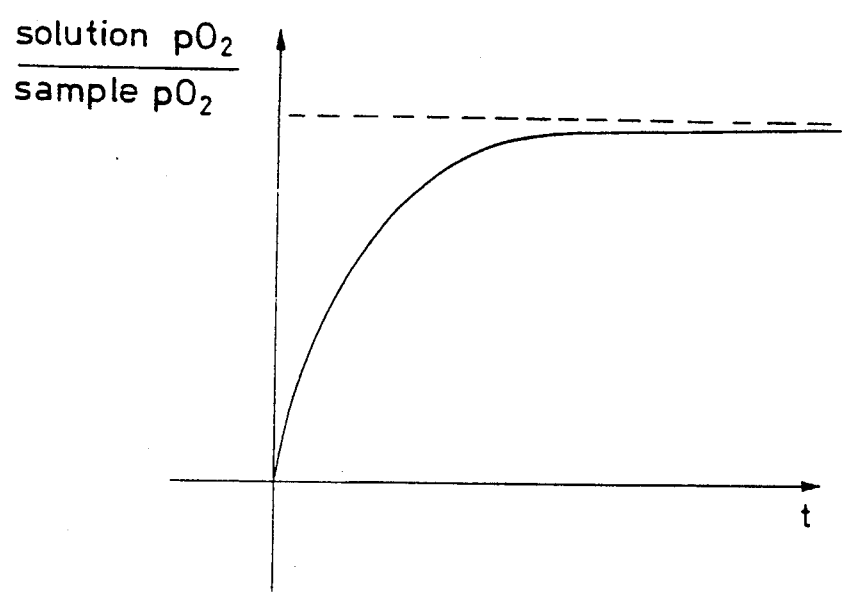
FIGS. 2, 3 and 4 are graphs showing the variation in certain parameters measured in the system of FIG. 1.

The diagram of FIG. 2 shows how the $pO_2$ in the solution can be considered to vary qualitatively as a function of the sample $pO_2$ and as a function of time. The vertical axis represents the ratio of solution $pO_2$ to sample $pO_2$ and the horizontal axis represents time. For measurement accuracy and as time is not a critical factor, the measurement solution is retained in the diffusion cell until the derivative of the function shown in FIG. 2 reaches a value sufficiently low to allow the usual tolerances on residence time to be considered negligible. For example, in general a residence time of 20 seconds can be considered sufficient, as a compromise between measurement accuracy and measurement speed. On termination of the permeation stage, the pump 15 pumps the measurement solution in the reverse direction, so that the quantity held in the diffusion cell 13 flows backwards into the measuring cell 17 which emits signal with a peak indicating the $pO_2$ reached by the measurement solution, which itself depends on the sample $pO_2$, as heretofore explained.

In contrast to the traditional Clark electrode used in oxygen determination, in which a stationary state for an electrochemical determination of polarographic type is created, the present measuring cell forms part of a flow system in which a voltametric measurement of a peak value is made and then related to the partial pressure of the oxygen contained in the tested blood sample.

Figure 3:
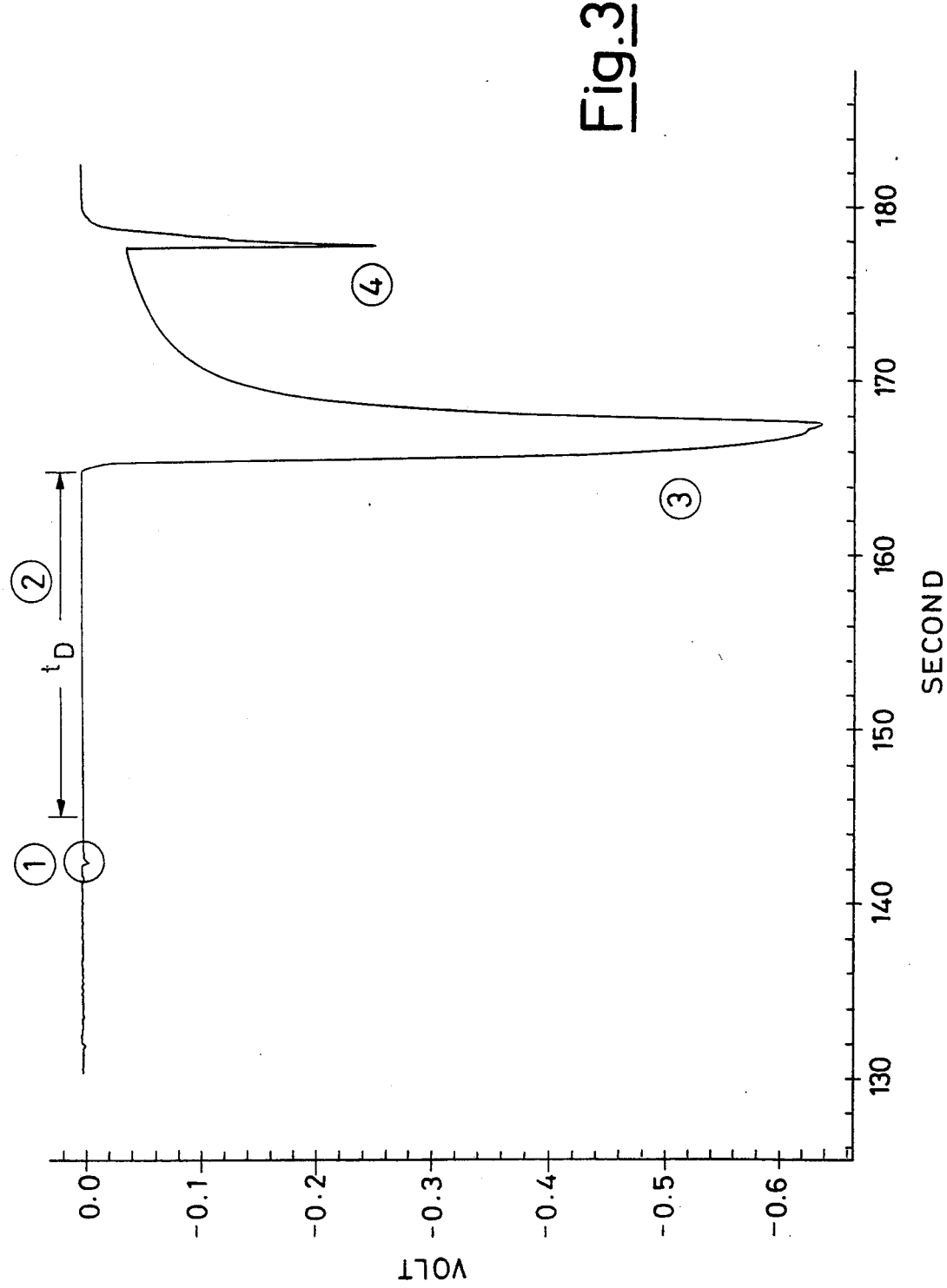
Figure 4:
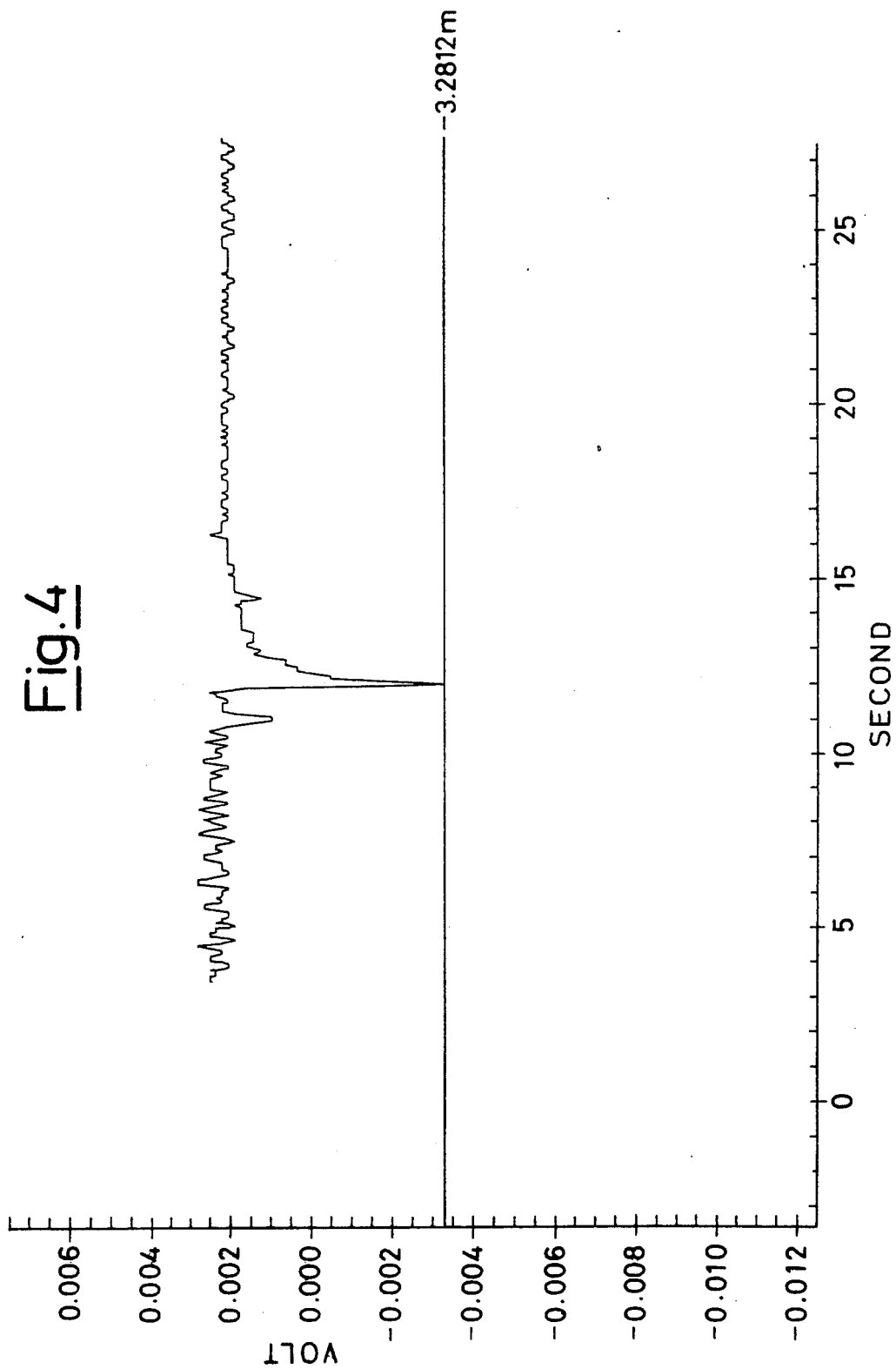

To indicate the type of signal which can be emitted by the voltametric measuring cell 17, FIG. 3 shows a typical signal pattern during reverse solution flow, which can be arrested after the peak has been measured.

During a measurement cycle the following stages occurring in time sequence can be specifically noted:

a) the hydrodynamic zero (circled and visible on an expanded scale in FIG. 3), which corresponds to the initial movement of the measurement liquid and enables proper operation of the catalytic reactor to be checked;

2) the section corresponding to the diffusion time to (about 20 seconds in the illustrated case);

3) the actual measurement stage, during which the measurement solution is transferred into the cell in which the electrochemical reduction in the dissolved oxygen is determined as a variation in current with time, suitably amplified and converted into voltage. The signal obtained in this manner contains information relating to the partial pressure of the oxygen contained in the sample measured;

4) the last even marked by a peak of smaller amplitude, corresponds to the renewal of measurement solution in the cell, indicated by a return to the base line value.

The maximum deviation of the measured dynamic signal from its initial value before fluid movement is preferably but not necessarily used to relate the conductivity change to the sample $pO_2$.

The processor unit 19 automatically makes the calculations required to obtain the $pO_2$ value of the sample.

The time within which the peak value is reached represents substantially an instrument constant and is therefore of diagnostic interest with regard to the correct operation of the instrument.

In this respect this quantification of the measurement time and the related quantification of the fluid movements within the fluid circuit makes it possible to check whether or not the entire apparatus is operating correctly, thus providing an operational check for the device on the basis of time.

It is important to note that in this manner the main object of the invention is attained, i.e., to restore the initial measurement conditions with absolute precision. In this respect, on beginning a new measurement, the pump 15 pumps oxygen-free measurement solution as far as the diffusion cell while at the same time discharging the solution contained in the circuit, this latter solution not offering the necessary guarantee of a $pO_2$ substantially of zero or close to zero within predetermined tolerances.

In order to obtain a substantially oxygen-free measurement solution, it has been found convenient to use an aqueous alcohol solution for feeding a catalytic reactor based on a metal belonging to the chemical group of the platinum (such as platinum, iridium, palladium, etc.).

In a preferred embodiment, not limiting the present invention, to produce a substantially oxygen-free solution it has been found particularly convenient to use a strongly alkaline aqueous alcohol solution of a primary alcohol (e.g., of 1-4 carbons) in deionized water, then propelling the solution to a catalytic reactor based on platinum supported on alumina.

EXAMPLE 1

The starting solution contained:

| | |
|---|---|
| methyl alcohol | 200 ml |
| NaOH | 0.1 N |
| Deionized H$_2$O | sufficient to reach 1 L |

This solution is clearly a strongly alkaline (NaOH) aqueous alcohol solution (H$_2$O/CH$_3$OH) moreover containing dissolved atmospheric oxygen (since the solution has been made in direct contact with the atmosphere).

Once it has been made, the solution was propelled by the pumping unit 15 to a catalytic reactor 16 made of platinum supported on alumina, having the function to remove the oxygen dissolved in the aqueous alcohol solution.

An employed catalyst has been, for example, the one sold by Aldrich (cat.31132-4) which exhibits a 5% platinum content with a 325 mesh granulometry. Approximately 0.75 g of such catalyst was packed into a stainless steel tubular reactor as described above. The catalyst was therefore contacted by the alkaline solution of water and methyl alcohol, and under these conditions the atmospheric oxygen dissolved in the solution acts as oxidizing agent for the dissolved methyl alcohol.

In this way the complete elimination of the oxygen is assured in the starting solution, which therefore becomes ready to be used in the fluidic channel as acceptor electrolyte for the oxygen coming from the blood sample to be tested. The absence of dissolved oxygen in the solution thus obtained has been detected by the measuring cell 17 which then will detect the oxygen content diffused in the fluidic channel by the blood sample.

The mentioned values, which have been identified as advantageous to obtain relevant results, must be considered not critical and they can be proportionally modified.

As primary alcohol, in addition to that above mentioned, can be mentioned ethanol or propyl alcohol. With these two alcohols have been obtained final solutions characterized by the lack of dissolved oxygen and therefore able to be advantageously used in the blood gas analyzer.

We claim:

1. A process for determining $pO_2$ in a blood sample, comprising
   a. propelling a measurement solution with substantially zero $pO_2$ along a fluid circuit wherein said solution passes in succession through a measuring cell to a diffusing cell;
   b. in the diffusion ell, halting the movement of said measurement solution and contacting the measurement solution with the blood sample to be tested via a permeation membrane which is permeable to gases but not to ions for a time sufficient to allow gases dissolved in the blood sample to diffuse through the membrane and into the solution;
   c. propelling the measurement solution in the reverse direction through the circuit to the measuring cell; and
   d. in the measuring cell, determining the value of an electrical quantity of the solution which is related to the $pO_2$ in the blood sample.

2. The process of claim 1, comprising the additional step of rendering the measurement solution substantially oxygen-free by passing it through a catalytic reactor in step (a) prior to passing it through the measuring cell.

3. The process of claim 2, wherein the catalytic reactor comprises a transition metal selected from the group consisting of platinum, iridium and palladium.

4. The process of claim 3, wherein the catalytic reactor comprises platinum supported on alumina.

5. The process of claim 1, wherein the measurement solution is an aqueous alcohol solution.

6. The process of claim 5, wherein the aqueous alcohol solution is an alkaline aqueous solution of a primary alcohol in deionized water.

7. The process of claim 1, wherein the measuring cell is a thin layer volumetric cell.

8. An apparatus for determining $pO_2$ in a blood sample, comprising
   a fluid circuit comprising (i) a source of a measurement solution having substantially zero $pO_2$, (ii) a measuring cell for determining the value of an electrical quantity of the solution passing through the cell related to the $pO_2$ of the blood sample, and (iii) a diffusion cell divided into two chambers by a permeation membrane which is permeable to gasses but not to ions in which the solution is brought into static contact with the blood sample via said permeation membrane;
   means for propelling the solution from the source along the circuit past the measuring cell and to the diffusion cell, and for propelling the solution in the reverse direction to the measuring cell; and
   means for measuring the value of the electrical quantity of the solution in the measuring cell.

9. The apparatus of claim 8, further comprising a catalytic reactor for rendering the measurement solution oxygen-free, said catalytic reactor being located in the fluid circuit between the source of measurement solution and the measuring cell.

10. The apparatus of claim 9, wherein the catalytic reactor comprises a transition metal selected from the group consisting of platinum, iridium and palladium.

11. The apparatus of claim 10, wherein the catalytic reactor comprises platinum supported on alumina.

12. The apparatus of claim 8, wherein the measurement solution is an aqueous alcohol solution.

13. The apparatus of claim 12, wherein the aqueous alcohol solution is an alkaline solution of a primary alcohol in deionized water.

14. The apparatus of claim 8, wherein the measuring cell is a thin-layer voltametric cell.

* * * * *